United States Patent [19]
Donis et al.

[11] Patent Number: 5,541,102
[45] Date of Patent: Jul. 30, 1996

[54] BOVINE CELL LINE RESISTANT TO IN VITRO INFECTION BY BOVINE VIRAL DIARRHEA VIRUS AND ALL OTHER KNOWN PESTIVIRUSES

[75] Inventors: Ruben O. Donis; Eduardo F. Flores, both of Lincoln, Nebr.

[73] Assignee: Board of Regents, University of Nebraska-Lincoln, Lincoln, Nebr.

[21] Appl. No.: 300,271

[22] Filed: Sep. 2, 1994

[51] Int. Cl.$^6$ ............... C12N 5/00; C12N 7/00; C12N 7/01; A61K 39/12
[52] U.S. Cl. ............... 435/240.2; 435/240.1; 435/235.1; 424/218.1
[58] Field of Search ............... 435/240.1, 240.2, 435/235.1; 424/218.1

[56] References Cited

PUBLICATIONS

ATCC Catalog 1988 6th Edition p. 16.
Am. J. Vet. Res. 1992. Kopp et al. Cytogentic Characterization of the . . . 53(9):1693–95.

*Primary Examiner*—James C. Housel
*Assistant Examiner*—N. M. Minnifield
*Attorney, Agent, or Firm*—Suiter & Associates PC

[57] ABSTRACT

Bovine cell line resistant to infection by the pestiviruses Bovine Viral Diarrhea Virus (BVDV), Hog Cholera Virus (HCV) and Border Disease Virus (BDV) and all progeny and mutants thereof. A bovine cell line (CRIB) that is resistant to infection by cytopathic and non-cytopathic BVDV and by other Pestiviruses due to a stable, recessive genetic defect which blocks infection at the level of viral entry.

4 Claims, No Drawings

BOVINE CELL LINE RESISTANT TO IN VITRO INFECTION BY BOVINE VIRAL DIARRHEA VIRUS AND ALL OTHER KNOWN PESTIVIRUSES

GOVERNMENT RIGHTS

The present invention was partially funded by CSRS contract #92-37204-7959.

A portion of the disclosure of this patent document contains material which is subject to copyright protection, The copyright owner has no objection to the facsimile reproduction by anyone of the patent document or the patent disclosure, as it appears in the Patent and Trademark Office patent file or records, but otherwise reserves all copyright rights whatsoever.

CROSS REFERENCES

Related Applications

The present application is an original patent application and is currently not known to be related to any co-owned and co-pending application.

TECHNICAL FIELD

The present invention is the first bovine cell line reported to be resistant to in vitro infection by bovine viral diarrhea virus (BVDV) and all other known viruses belonging to the genus Pestivirus. These cells, designated CRIB cells (cells resistant to Bovine Viral Diarrhea Virus) may be useful tools for studying the early interactions of pestiviruses with host cells. Furthermore, CRIB cells may have important applications in basic research, diagnostic virology and for production of BVDV-free biologicals in bovine cells.

BACKGROUND ART

Bovine viral diarrhea virus (BVDV) is an enveloped virus of cattle with a single-stranded RNA genome 12.5 kb in length. The naked viral RNA is infectious upon transfection into permissive cells, being translated into a single 3988 amino acid polyprotein that is co- and post-translationally processed by viral and cellular proteases. BVDV is currently classified within the Flaviviridae family, being a member of the genus Pestivirus, along with the hog cholera virus (HCV) and border disease virus (BDV).

Bovine viral diarrhea virus naturally infects cattle, ovine, swine, caprine, buffalo and a wide variety of wild ruminants, all members of the order Artiodactyla. BVDV replicates in tissue culture cells from these species and has been often found contaminating cells from other non-related species. All known bovine cell lineages and primary cultures are susceptible to BVDV infection in vitro. In contrast, only selected cell populations have been shown to be infected in vivo. The reasons for the difference between the narrow tissue tropism in vivo and the wide cell range in vitro are not understood, but constitute a fundamental issue for the understanding of viral pathogenesis. It is likely that this difference in tissue tropism is derived from differential expression of host cell molecules that modulate virus replication and spread. The identification of host cell factors modulating virus replication may lead to the understanding of the molecular basis of virus host range and tropism.

The detailed mechanism(s) of BVDV entry into susceptible cells are unknown but certain general aspects have been elucidated. Some evidence suggests that BVDV, like other members of the Flaviviridae, initiate infection by a mechanism of receptor-mediated endocytosis, followed by low pH-dependent fusion of the virus envelope with the endosomal membrane. The BVDV envelope glycoproteins EO (gp 48) and/or E2 (gp 53) are believed to participate in the initial interactions of virions with cells. The major glycoprotein E2 (gp 53) is likely to play a major role in attachment/penetration since most monoclonal antibodies directed against E2 are neutralizing. Cell surface molecule(s) interacting with viral envelope glycoproteins to bring about BVDV entry have not been identified and characterized. Monoclonal antibodies directed against bovine cell surface proteins have been shown to partially inhibit BVDV infection, but their molecular specificity remains unknown. In addition, anti-idiotypic antibodies mimicking the BVDV E2 (gp 53) have been shown to partially prevent infection with some strains of BVDV in MDBK cells (Xue & Minocha, 1993, "Identification of the cell surface receptor for bovine viral diarrhea virus by using anti-idiotypic antibodies." *J. Gen. Virol.* 74: 73–9). These data taken together suggest that multiple receptors or BVDV may exist and that different strains may use different receptors to initiate infection (Collett et al., 1989 "Comparisons of the pestivirus bovine viral diarrhea virus with members of the flaviviridae." *J. Gen. Virol.* 69:2637–43; Xue & Minocha, 1993, supra).

Hog cholera virus (HCV, also known as classical swine fever in European countries) is a member of the genus Pestivirus, within the family Flaviviridae, as described in the 5th Report of the International Commission on Taxonomy of viruses. The virus shares a number of biological properties with the other two members of the genus: BVDV of cattle and Border Disease Virus of sheep. They have similar host ranges in vivo and in vitro. They may also cause transplacental infections in heterologous hosts; e.g. BVDV can infect pigs and HCV may infect cattle. However, infection of heterologous animal hosts with a Pestivirus does not result in acute disease. The overall genetic relatedness among the Pestiviruses is well defined by the extent of nucleotide sequence homology between the genomes of the virus species in this genus: 60–70%. Some strains of HCV are highly virulent, and can cause extremely high mortality rates in susceptible swine populations. This virus was eradicated from the U.S. in the 1970's. Harkness, J. W. (1985), "Classical swine fever and its diagnosis: A current view." *Vet. Rec.* 288–293; Collett, M. S., Moennig, V., and Horzinek, M., "Recent advances in Pestivirus Research." (1989) *J. Gen. Virol.,* 70:253–266.

Border disease virus of sheep is a Pestivirus responsible for the hairy-shaker syndrome in lambs, also known as Border Disease. The syndrome is a consequence of the fetal infection which causes congenital neurologic and tegument defects. The virus appears to be unable to cause severe acute disease, in contrast with the bovine and swine Pestiviruses. Moennig, V., "Pestiviruses: A Review." *Vet. Microbiol.* 23(1–4): 35–54. The virus is present in the U.S. but its economic importance is commensurate with that of the sheep industry. The biology of the Border Disease virus is similar to that of BVDV, sharing ~70% nucleotide sequence homology between genomes. P. Becher, et al "Molecular Characterization of Border Disease Virus, a Pestivirus From Sheep." *Virology* (1994) 198:542–51.

In 1988, House, USDA, et al reported a porcine kidney cell line IB-RS-2 Clone D10 (IB-RS-2 D10) which was said to be resistant to infection by both hog cholera virus (HCV) and BVDV (House, et al, 1988, "Characteristics of the Porcine Kidney Cell Line IB-RS-2 Clone D10 (IB-RS-2 D10) Which is Free of Hog Cholera Virus" *In Vitro Cell. Dev. Bio.* 24:677–682). After cloning, it was tested extensively and judged to be free of HCV based upon the results of the tests available at that time. Based on these results, USDA authorized ATCC to distribute IB-RS-2 D10. However, in 1993, as part of an ongoing program to test cell lines for the presence of Bovine Viral Diarrhea Virus, ATCC tested this cell line and found it to be infected with HCV. It is believed that the parent cell line from which the D10 clone was derived was itself infected with HCV and the cloning performed by House reduced the HCV to levels that were not detectable by the tests performed at that time, but with subsequent passages, the virus multiplied to the point where it became detectable. The resistance to BVDV infection exhibited by the D10 clone is not a true resistance. Instead, the presence of hog cholera virus in the D10 cell caused the cell to exhibit interference when the cells are inoculated with a cytopathic BVD virus. The cytopathic effect was delayed and the viral titer was low after infection. The viral interference phenomenon exhibited by the host cholera virus in IB-RS-2 D10 line accounts for its apparent "resistance" to BVDV infection. However, the phenomena of interference is not the same as a cell line being refractory to infection with BVDV. (See Malmquist, et al., "Interference of Bovine Viral Diarrhea Virus by Hog Cholera Virus in Swine Kidney Cell Cultures." *Am. J. Vet. Res.* 26(115):1316–1327 (1965).) Therefore, while efforts have been made to identify a cell line resistant to in vitro BVDV infection, these efforts have failed heretofore.

DISCLOSURE OF INVENTION

We have isolated, cloned and characterized a novel bovine cell line, referred to as CRIB, that is resistant to infection with BVDV and all other known viruses of the genus Pestivirus. The clone designated CRIB-1 was deposited at the American Type Culture Collection (Rockville, Md.) on Jul. 6, 1993 under Accession No. SD 1831. CRIB cells were derived from the well characterized Madin-Darby Bovine Kidney (MDBK) cell line (ATCC, CCL-22) through cloning of cells surviving multiple rounds of infection with a highly cytolytic BVDV strain. The selected clones were shown to be free of infectious BVDV or subviral products by indirect immunofluorescence, cocultivation, animal inoculation, northern and southern blot hybridization and RNA PCR. Repeated challenge of CRIB cells with several cytopathic and non-cytopathic BVDV strains does not result in infection as demonstrated by immunofluorescence and cocultivation. Challenges made with isolates of hog cholera virus and border disease virus, the other known members of the Pestivirus genus, also did not result in infection. Microsatellite DNA PCR, karyotyping and isoenzyme analysis have demonstrated that CRIB are genuine bovine cells. CRIB cells are susceptible to other bovine viruses like the parental MDBK cells. The genetic defect of CRIB cells is stable and recessive: somatic cell hybrids of CRIB with bovine lymphocytes are susceptible to BVDV infection and produce infectious virus. Transfection of CRIB cells with BVDV RNA or virus inoculation in the presence of polyethyleneglycol (PEG) result in productive infection. Therefore, the defect of CRIB cells is at the level of virus entry.

Therefore, it is a primary object of the present invention to provide a bovine cell line resistant to in vitro BVDV infections and to infection by all other known viruses of the genus Pestivirus. Another object of the present invention is to provide cells which may be utilized to study the early interactions between pestiviruses and their host cells. Yet another object of the present invention is to provide CRIB cells which may be utilized in diagnostic virology to identify the host factors mediating BVDV infection as well as for production of BVDV-free biologicals in bovine cells. These cells may also be used to clone the cellular molecule required for entry of BVDV, hog cholera virus and border disease viruses into cells. These and other objects will be apparent to the art upon reading the specification.

DETAILED DESCRIPTION

Experimental Procedures to Assay Resistance to BVDV

The results of experiments presented herein and summarized in Table 1 below indicate that the resistance exhibited by the CRIB cell line is the result of the absence of a common cell surface factor that is required to mediate virus entry/uncoating by most, if not all, BVDV strains in MDBK cells.

TABLE 1

Methods used to detect infectious
BVD virus and viral products in CRIB cells.

| Assay | Result |
| --- | --- |
| Indirect Immunofluorescence (IFA)' | Negative |
| Cocultivation | Negative |
| Animal inoculation | Negative |
| Northern Blot | Negative |
| Southern Blot | Negative |
| RNA PCR | Negative |

1. Cells and Viruses

Madin-Darby Bovine Kidney (MDBK, CCL-22) cells were obtained from the American Type Culture Collection (ATCC, Rockville, Md.) at passage 110 and routinely cultured for approximately 25 passages. The source of other cell lines used in the BVDV host range experiments is shown in Table 2. Cells were maintained in Eagle's minimum essential medium (MEM) (Gibco Labs, New Island, N.Y.) supplemented with 5% fetal horse serum (Sigma Chem. St. Louis, Mo.), penicillin and streptomycin (Sigma Chem.). BL-3 cells were cultured in RPMI medium supplemented with 10% of gamma-irradiated fetal bovine serum (Gibco Labs).

The source of the BVDV isolates is shown in Table 3. Stocks of BVD virus were produced in bovine testicle cells, quantitated and stored at −70° C. The other bovine viruses were obtained from the Veterinary Diagnostic Laboratory, University of Nebraska Lincoln, Lincoln, Nebr.

2. Monoclonal Antibodies (Mabs) and Immunofluorescence Assays

Murine monoclonal antibodies (mabs) 4, 12, 19 and 20 are specific for distinct epitopes of the major BVDV envelope glycoprotein gp 53 (E2) and mab 15 is specific for the envelope glycoprotein gp 48 (EO) (Donis & Dubovi, 1987). Bovine anti-BVDV polyclonal antisera was produced as previously described (Donis & Dubovi, 1987). Fluorescein isothiocyanate (FITC)-conjugated antibovine parvovirus antisera was obtained from the National Veterinary Services Laboratory (NVSL, Ames, Iowa).

Indirect immunofluorescence (IFA) for BVDV antigens was performed using a mixture of mabs 4, 12, 15, 19 and 20 (oligoclonal) or polyclonal antisera as primary antibody and a FITC-conjugate goat anti-mouse or anti-bovine IgG monoclonal antibody (Boeringher Manhein, Inc.) as secondary antibody. IFA was performed 24 hours post-infection (hpi)

for cytopathic and 36 hpi for non-cytopathic BVDV strains. Direct immunofluorescence of cells inoculated with bovine parvovirus was performed 48 hpi.

3. BVDV Infection and Cloning of Surviving MDBK Cells—Establishment of a Bovine Cell Line Resistant to Bovine Viral Diarrhea Virus Infection MDBK cells ($5 \times 10^6$) were infected with approximately 10 $TCID_{50}$/cell of a cytopathic BVDV strain (Singer-cp) and medium was changed every 3 days until survivor cells grew up to form colonies (approximately 6 weeks). Infection of bovine cells with cytopathic BVDV at high m.o.i. usually results in lysis of nearly 100% of the cells. However, occasional surviving cells may give rise to a persistently infected culture. Following infection of MDBK cells with m.o.i. of 10 $TCID_{50}$ of BVDV Singer-cp, a few cells survived and were cultured for six weeks until they formed colonies and could be trypsinized and subcultured. During this time, the cells alternated periods of growth with periods of crisis in which nearly the entire monolayer showed characteristic BVDV-induced vacuolation and died. Throughout several periods of growth and crisis, some cell lineages were being selected that no longer showed cytopathology and grew up to form colonies. Indirect immunofluorescence (IFA) performed at the time of the first subculture showed that almost the totality of the cells were negative for BVDV antigens. To test the susceptibility of the cells lacking BVDV antigens, the cells were re-infected with BVDV Singer-cp and processed for IFA. After confirmation that the cells devoid of BVDV antigens were resistant to infection with BVDV, they were cloned out by limiting dilution and 20 independent clones were obtained. The survivor cells, designated CRIB (Cells resistant to Infection with BVDV), were cloned out by limiting dilution and clones derived from a single cell were propagated. Twenty clones, named CRIB-1 to 20, were selected, propagated and stored in liquid nitrogen. The initial experiments performed to detect BVDV antigens by IFA and cocultivation were carried out with the uncloned population of cells and with all twenty clones (CRIB-1 thru CRIB-20). The subsequent experiments utilized the cells from clone 1 (CRIB-1).

4. Assays for the Detection of Infectious BVD Virus and Viral Subproducts in CRIB Cells Show that CRIB Cells Contain no Infectious BVD Virus or Viral Subproducts As CRIB cells were derived from cells that survived infection with BVDV and had been cultured in the presence of virus for up to six weeks, it would be expected that they might still support low levels of virus replication or contain residual viral RNA. Therefore, the resistance to infection could be explained by the presence of replication-competent viral RNA that would interfere with replication of the homologous virus. Different approaches were taken to investigate if CRIB cells contain infectious virus or vital remnants. The presence of BVDV antigens in CRIB cells was monitored by IFA as described above. Production of infectious virus by CRIB cells was assessed by cocultivation with indicator bovine testicle cells and animal inoculation: (a) Cocultivation: CRIB and bovine testicle cells were trypsinized, mixed in a ratio of 1:1 and cultivated for up to 4 weeks. Cells were subcultured twice a week and production of BVDV antigens was monitored by IFA using a mixture of BVDV-specific monoclonal antibodies. Indirect immunofluorescence (IFA) using polyclonal antisera and a panel of monoclonal antibodies against structural and non-structural proteins has failed to detect BVDV antigens in these cells. Likewise, cocultivation of CRIB with bovine testicle cells for up 4 weeks did not reveal production of infectious virus. (b) Animal inoculation: approximately $2.5 \times 10^7$ CRIB-1 cells were inoculated intravenously in an eight months-old, BVDV-seronegative calf. Blood samples for serology were taken before inoculation and 2 and 4 weeks post-inoculation. Heat inactivated (56° C. for 30 minutes) serum samples were submitted to serum-neutralization assays as described elsewhere (Rossi & Kiesel, 1971 ). The serum-neutralization assays performed on blood samples collected 4 weeks after inoculation showed that the animal remained seronegative for BVDV attesting to the lack of production of infectious BVD virus by CRIB cells.

CRIB cells were also shown to be free of residual BVDV genetic material (RNA) by means of northern blot and RNA PCR. Also, a possible integration of DNA copies of the viral RNA into the cell chromosomes was investigated by southern blot hybridization, giving negative results. (a) Northern blot: total RNA extracted from CRIB-1, BVDV-infected and mock-infected MDBK cells was separated in a denaturing 1% agarose gel, blotted onto a nitrocellulose membrane, prehybridized and hybridized according to standard protocols (Ausubel et al., 1986). (b) Southern blot: CRIB-1 and MDBK genomic DNA was extracted by a salting out method (Miller et al., 1988), digested overnight with 2 U/Mg of EcoRI, BamHI and HindIII (Promega) electrophoresed in an 1% agarose gel and blotted onto a nitrocellulose membrane. Prehybridization and hybridization were performed as previously described (Ausubel et al., 1986). The nitrocellulose membranes were hybridized with $^{32}P$ labeled DNA probe ($\alpha$dATP, Amersham, Inc.) synthesized by random priming (Feinberg & Vogelstein, 1983) of a 1531 bp HindIII/BglII DNA fragment of the plasmid PBSD 2.3 that corresponds to the NS5 (p75) region of the BVDV NADL strain (Collet et al., 1988) and exposed to a Kodak-X-Omat film. (c) RNA PCR: A set of two 14-mer primers was used to amplify a target sequence of 323 bp from the p75 region of the BVDV genome. Total cellular RNA from approximately $5 \times 10^5$ CRIB-1, BVDV-infected and mock-infected MDBK cells, contained in 2 $\mu$l, were used as template. Total cell RNA was extracted as described below and reverse transcription was performed as previously described (Lopez et al., 1991 ) using avian myeloblastosis virus (AMV) reverse transcriptase (Life Sciences, Inc.). The PCR conditions were as follows: 1 minute denaturation at 95° C.; 1 minute annealing at 34° C. and 3 minutes extension at 56° C. in a total of 35 cycles. PCR products were analyzed by agarose gel electrophoresis in a ethidium bromide-stained 1% agarose gel. Specificity of RNA PCR amplification was ascertained by southern blot hybridization, using the same probe described above.

Taken together, these results demonstrate that CRIB cells are free of BVD virus or viral subproducts. Furthermore, the lack of detection of residual BVDV RNA indicates that resistance to infection is not derived from homologous interference.

5. Assays for BVDV Susceptibility Show that CRIB Cells are Resistant to BVDV Infection Initially, CRIB-1 and MDBK cells were inoculated with BVDV Singer-cp and VS115ncp at multiplicities of infection (m.o.i.) ranging from 1 to 100 $TCID_{50}$. Infection was monitored by indirect immunofiuorescence (IFA) and by passage of supernatant of cultures in bovine testicle cells. Production of infectious virus by CRIB-1 cells following inoculation with BVDV Singer-cp and VS115-ncp was further monitored by cocultivation with indicator bovine testicle cells. Cocultivation was performed as described above with the following modifications: after adsorption of the virus inoculum for one hour at 37° C. and washing unbound virus, remaining extracellular virus was neutralized by addition of a mixture of neutralizing mabs or anti-BVDV polyclonal antisera for 72 hours. Following extracellular virus neutralization, CRIB-1 cells were trypsinized, mixed and cultured with bovine testicle cells. The cocultures were maintained up to 2 weeks and infection of indicator cells was monitored by IFA. Infected MDBK cell controls were included to ascertain the inability of the neutralization step to clear intracellular virus in infected MDBK cells.

The BVDV inoculation experiments, using Singer-cp and VS115-ncp at m.o.i. ranging from 0.1 to 100 $TCID_{50}$, were repeated multiple times and CRIB cells have been consistently shown to be refractory to BVDV infection (Table 2). Inoculation of CRIB cells with these BVDV strains at m.o.i. of approximately 10 $TCID_{50}$ did not cause appearance of infected cells when tested by IFA. In addition, we were unable to detect production of infectious virus by $10^7$ CRIB cells after inoculation of 1 $TCID_{50}$ of VS115ncp followed by cocultivation with susceptible cells.

TABLE 2

Susceptibility of MDBK and CRIB cells to infection with bovine viral diarrhea virus (BVDV)

| Strain/Isolate | Reference/origin | Biotype | MDBK | CRIB |
|---|---|---|---|---|
| Singer | McClurkin, 1974 | cp | + | − |
| NADL | Gutenkust & Malmquist, 1964 | cp | + | − |
| Cpl | Meyers at al, 1991 | cp | + | − |
| NCP-1 | Meyers et al, 1991 | cp | + | − |
| VS115 | Donis, unpublished | ncp | + | − |
| VS14a | Nebraska | ncp | + | − |
| VS8a | Dubovi, unpublished | ncp | + | − |
| VS83 | Dubovi, unpublished | cp | + | − |
| VS53a | Dubovi, unpublished | cp | + | − |
| VS22 | Oregon | cp | + | − |
| VS186 | Dubovi, unpublished | cp | + | − |
| VS60 | Maryland | cp | + | − |
| VS2 | Tennessee | cp | + | − |
| VS21 | Bolin, AJVR. 52: 1033 | cp | + | − |
| VS15 | Bolin, AJVR 52: 1033 | ncp | + | − |
| VS84 | Dubovi, unpublished | cp | + | − |
| VS91 | Dubovi, unpublished | cp | + | − |
| VS46 | Dubovi, unpublished | cp | + | − |
| VS110 | Dubovi, unpublished | cp | + | − |
| VS182 | Dubovi, unpublished | ncp | + | − |
| VS183 | Dubovi, unpublished | ncp | + | − |
| VS184 | Dubovi, unpublished | ncp | + | − |
| VS191 | Donis, unpublished | ncp | + | − |
| VS192 | Donis, unpublished | ncp | + | − |

Inoculation experiments using m.o.i. of 50 or higher occasionally resulted in detection of rare IFA positive CRIB cells. The frequency of infection of CRIB cells upon challenge with 50 TCID50/cell of cytopathic BVDV strains has been estimated to be around $10^{-6}$. These occasional infected cells appear not to transmit virus by cell-to-cell spread since no infected cell foci were found. This indicates that a very high m.o.i. is required to obtain a few infected cells but amplification of virus by multiple cycles of infection does not take place. Nonetheless, it is possible that occasionally infected cells may produce infectious virus that would eventually be detected by cell inoculation or cocultivation.

To ascertain the range of resistance of CRIB cells to different strains, CRIB-1 and MDBK cells were inoculated with each of the 24 BVDV isolates, including prototype strains and field isolates at a m.o.i. of approximately 1, and infection was monitored by IFA, using oligoclonal mabs, as described above (Table 2). We were unable to detect BVDV antigens in CRIB cells by IFA following inoculation with any of the BVDV isolates tested.

These results taken together demonstrate that CRIB cells are resistant to BVDV infection. CRIB cells are approximately $10^6$ more resistant to BVDV infection than their parental MDBK cells. Neither viral protein synthesis nor production of infectious virus have been detected in CRIB cells upon virus inoculation, thus we consider this cell line to be resistant to BVDV infection. The approximately $10^{-6}$ frequency of infection represents artifactual paths of virus entry when very high m.o.i.s are used. Furthermore, no one of the 24 isolates tested was able to infect CRIB cells, yet infecting more than 75% of MDBK cells, suggesting that the BVDV resistance in CRIB cells is not a virus strain-dependent phenotype.

6. BVDV in Vitro Host Range

To determine if the BVDV resistant phenotype of CRIB cells represents a unique event among bovine and cell lines from closely related species (order Artiodactyla), we performed BVDV infection experiments including different primary and established cell lines from these species (Table 3).

A number of primary or established cell lines of bovine and non-bovine origin were inoculated with approximately 1 $TCID_{50}$/cell of each of 6 BVDV strains and infection was monitored by IFA and passage of culture supernatant. BVDV- and mock-infected MDBK cells were used as controls. The results of this BVDV in vitro host range trial are shown in Table 3. The frequency of positive cells by IFA ranged from about 3–5% in swine PK-15 cells infected with cp BVDV to over 80% for almost all bovine cells infected with any of the strains. Ovine and goat cells were susceptible at levels comparable to those of bovine cells. Interestingly, primate (CV-1 and Veto) and feline cells (CRFK) were also found to be permissive to expression of BVDV antigens.

TABLE 3

Susceptibility of cells of species from the order Artiodactyla to bovine viral diarrhea virus (BVDV) infections[a]

| cell | species | organ | type | source |
|---|---|---|---|---|
| BL | bovine | lung | primary | VDC[b] |
| BT | bovine | nasal turbinate | cell line | VDC[b] |
| RD-420 | bovine | testicle | SV40 transf. | RD[c] |
| RD-9 | bovine | testicle | primary | RD[c] |
| MDBK | bovine | kidney | cell line | ATCC[e] |
| CPA-47 | bovine | endothelium | cell line | ATCC[e] |
| EbTr | bovine | trachea | cell line | ATCC[e] |
| A4 | bovine | adrenal | primary | GD/CJ[d] |
| Bi | bovine | brain | primary | GD/CJ[d] |
| C3 | bovine | cerebellum | primary | GD/CJ[d] |
| BI-3 | bovine | lymphocyte | BLV transformed | JR[f] |
| Lymphocytes | bovine | lymphocyte | primary | RD[c] |
| PT | swine | testicle | cell line | ATCC[e] |
| PK-1 | swine | kidney | primary | VDC[b] |
| PK-15 | swine | kidney | cell line | ATCC[e] |
| GT | caprine | testicle | cell line | ATCC[e] |
| ESLCH | caprine | esophagus | cell line | ATCC[e] |
| MDOK | bovine | kidney | cell line | ATCC[e] |

[a] As determined by indirect immunofluorescence at 20–24 h post infection for cp BVDV and 30–36 h for ncp BVDV using oligoclonal antisera as primary antibody and FITC conjugated anti-mouse IgG monoclonal antibodies as secondary antibody.
Origin of cells:
[b] Veterinary Diagnostic Center, UNL, Lincoln, NE.
[c] our laboratory;
[d] Drs. Gustave Delphon and Clinton Jones, DVBS, UNL, Lincoln, NE;
[e] American Type Tissue Collection, ATCC, Rockville, MD;
[f] Dr J. Ridpath, NADC, USDA, Ames, IA.

These and previous data confirm the assertion that virtually all bovine cells and cells from animals of the order Artiodactyla, regardless the tissue of origin, are susceptible to BVDV infection in vitro. Therefore, the resistance of CRIB cells to BVDV infection appears to represent a unique event among in vitro cultured cells from bovine and related animal species.

Crib Cells are Also Resistant to Other Known Pestiviruses

Having determined that CRIB cells were resistant to infection by BVDV, we then explored the permissiveness of these cells to other virus species in the genus Pestivirus, namely Hog Cholera Virus and Border Disease Virus.

MDBK and PK-15 cells were obtained from the American Type Tissue Collection (ATCC) and clone #1 (CRIB-1) was used exclusively in hog cholera experiments. Three border disease virus (BDV) isolates (Coos Bam, Id. and 31) were obtained from the University of California at Davis and the other isolate (BDV 264) was obtained from the Veterinary Diagnostic Laboratory of the University of Nebraska at Lincoln. The two hog cholera virus (HCV) strains (250 and 9202) were obtained from the National Veterinary Services Laboratory at Ames, Iowa. These are standard strains used routinely for serum neutralization assays.

Detection of BDV antigens was performed by indirect immunofluorescence (IFA), using a murine anti-pestivirus non-structural protein p80 (mab 20.10.6) as primary antibody and a FITC-conjugate goat anti-mouse IgG monoclonal antibody as secondary antibody. Detection of HCV antigens was performed by direct immunofluorescence using a goat anti-HCV FITC-conjugate polyclonal antisera.

CRIB-1 and MDBK cells were inoculated with BDV (Coos Bam, Id., 31 or 264) at a m.o.i. of approximately 1 and infection was monitored by IFA. MDBK cells served as positive control for BDV infection. The inoculation of CRIB-1 cells did not result in production of viral proteins as demonstrated by negative immunofluorescence. In contrast, approximately 70% of the MDBK cells inoculated with BDV were positive by IFA.

CRIB-1, MDBK and PK-15 cells were inoculated with HCV (250 and 9202) at a m.o.i. of 1. Infection was monitored by direct immunofluorescence performed 48 hours post-infection. PK-15 and MDBK cells served as positive controls for HCV infection. The inoculation of CRIB cells with the two isolates of hog cholera virus (HCV) at m.o.i. of approximately one did not result in production of viral proteins, as demonstrated by direct immunofluorescence performed 48 hours post-infection. Approximately 60 to 70% of PK-15 and MDBK cells were positive for HCV antigens in this experiment.

These results indicate that CRIB cells are resistant to infection with BDV and HCV, since no vital proteins are detected by IFA following inoculation with these viruses.

Characteristics of Crib Cells

1. CRIB Cells are Susceptible to Other Unrelated Viruses

In order to investigate whether the resistant phenotype was BVDV-specific or consequence of a non-specific antiviral blocking activity, CRIB cells were inoculated with several bovine viruses that are not of the genus Pestivirus. CRIB-1 and MDBK cells were infected with approximately 1 $TCID_{50}$ of bovine herpesvirus type 1,2 and 4 (BHV-1, 2 and 4), bovine adenovirus type 3, vesicular stomatitis virus (VSV), bovine parvovirus (BPV), bovine respiratory syncytial virus (BRSV), bovine enterovirus and bovine parainfluenza-3 virus (PI-3). Infection with BPV was monitored by immunofluorescence 48 hours post-inoculation (hpi) and infection with the other viruses was assessed by appearance of cytopathic effect (CPE) 24 to 48 hpi. Supernatant of these cultures was harvested and progeny virus production was quantitated by infection of bovine testicle cells with serial 10-fold dilutions and expressed as 50% tissue culture infectious dose ($TCID_{50}$)(Reed & Muench, 1956). Plaque formation by vesicular stomatitis virus (VSV) in MDBK and CRIB cells was assayed as described by Wunner. Wunner, W. H. (1985), *Virology, a practical approach*, pp. 79–93 (B. W. J. Mahy, Ed., Oxford/Washington, D.C.: IRL Press).

The outcome of the infection of CRIB cells with each of these viruses was compared with that in the parental MDBK cells. The course of the infection, cytopathology and yield of most of these viruses in CRIB cells did not differ significantly from those observed in MDBK cells. Plaques formed by VSV and BHV-1 in CRIB cells were morphologically similar to those formed in MDBK cells. A significant reduction in yield of progeny BRSV was observed in CRIB -1 as compared with MDBK cells. Nonetheless, the susceptibility of CRIB cells to five other bovine viruses indicates that the resistant phenotype is due to a specific anti-BVDV property rather than to a non-specific viral replication block.

2. Assays for the Species Origin of CRIB Cells Show that CRIB Cells are Genuine Bovine Cells The ineditism of a bovine cell resistant to BVDV infection prompted us to investigate whether these cells were indeed of bovine origin. That CRIB cells are genuine bovine cells was confirmed by microsatellite DNA PCR, karyotyping and isoenzyme analysis. Microsatellite DNA PCR of CRIB-1 cells using primers specific for ruminant sequences showed a pattern of amplification compatible with bovine or ruminant species, ruling out a possible primate, canine, rodent or equine cell contamination which would be BVDV resistant. Karyotyping of CRIB-1 cells has revealed a modal distribution of chromosomes virtually identical to the parental MDBK cells. Chromosomes had typical bovine morphology, similar to primary bovine testicle cells at passage 8. Moreover, isoenzyme analysis has shown that the gel mobility of a set of enzymes of CRIB cells is identical of that of the parental and other bovine cells. The enzymes analyzed were glucose-6-phosphate dehydrogenase (G6PD), lactate dehydrogenase (LDH), nucleoside phosphorylase (NP), malate dehydrogenase (MD), mannose phosphate isomerase (MPI), peptidase B (Pep B) and glutamate oxalacetate transaminase (AST/GOT). The gel mobilities of these enzymes reflect species-specific patterns of post-translational modifications and have been reliable parameters used to identify the species' origin of cell lines.

Taken together, these results conclusively show that CRIB cells are genuine bovine cells and not a cell contaminant from other animal species.

3. Fusion of CRIB with Bovine Lymphocytes Render them Susceptible to BVDV Infection Fusion of CRIB cells with bovine lymphocytes (BL-3) to generate heterokaryons was performed to address two questions: (1) is there a dominant negative intracellular block for BVDV replication in CRIB cells? and (2) is it possible to complement the CRIB resistant phenotype by wildtype gene expression? To answer these questions, somatic cell hybrids (heterokaryons) were produced by fusion of CRIB cells and bovine lymphocytes (BL-3). CRIB-1 cells ($10^7$) were fused with approximately $10^8$ bovine lymphocytes (BL-3), using 50% (w/v) polyethylene-glycol(PEG) (MW1450, ATCC) according to fusion protocols previously described (Pontecorvo, 1975). After fusion, the cells were seeded in 12 well plates, left to attach overnight and unattached cells were removed by washing the cultures three times with PBS.

Cultures were inoculated with BVDV Singer-cp and VS 115-ncp (10 TCID50/cell) one to 10 days after fusion and infection was monitored by IFA. Production of infectious virus by BL-3/CRIB-1 hybrids infected with VS115-ncp was assessed by cocultivation with bovine testicle cells as described above. PEG-fused CRIB-1 cells and unfused cocultures of BL-3 and CRIB cells were used as controls. BL-3 cells grow in suspension and can be easily washed out from the culture after attachment of CRIB cells. Therefore, cells attached to the plastic surface would be either unfused CRIB cells or hybrids/heterokaryons that express the CRIB phenotype for anchorage-dependent growth. BVDV inoculation of CRIB/BL-3 fused cells at different time points after fusion showed a significative number of positive cells. These positive cells were detected upon challenge performed up to 10 days after fusion. Cocultivation of BVDV-inoculated hybrids with indicator cells was followed by recovery of infectious virus showing that the fused cells support the complete viral cycle. In contrast, virus inoculation of control CRIB cells subjected to fusion did not result in detection of viral proteins or progeny virus.

These results demonstrated that there is not a negative dominant block for BVDV replication in CRIB cells since hybrids (or heterokaryons) are susceptible to infection. More importantly, they suggested that the resistant phenotype of CRIB cells is a recessive trait since expression of genes from wildtype cells render them susceptible to BVDV infection.

4. CRIB Cells are Defective in BVDV Entry and in Entry of Other Known Pestiviruses (a) BVDV Entry The lack of detection of viral proteins following inoculation of CRIB cells with BVD virus first suggested that the virus replication block involves an early stage of the vital cycle, preceding translation of the input RNA genomes. If the resistant phenotype were derived solely from a block in the viral entry, bypassing this step would allow productive vital replication. We addressed this hypothesis by performing two sets of experiments: (1) transfection of BVDV RNA into CRIB cells, and (2) addition of polyethylene-glycol (PEG) to the vital inoculum, trying to overcome a possible defect in virus entry.

(i) BVDV RNA Isolation and Transfection Assays

Bovine testicle and MDBK cells were infected with 5 p.f.u/cell of Singer-cp and harvested for RNA isolation 20 hours post infection. CRIB-1 and mock-infected MDBK cells were processed in parallel for northern blot analysis. Total cellular RNA was extracted as previously described (Ausubel et al., 1986). Viral RNA was separated from total cellular RNA by agarose gel electrophoresis and isolated from the gel by adsorption to glass powder. The RNA used for transfection consisted of approximately 1 pg of agarose-gel purified viral RNA and 5 pg of carrier RNA per well.

Transfection of BVDV RNA was performed in 60% confluent CRIB-1 and MDBK cells grown in 12 well plates (approximately 6×10 cells/well). Transfection was performed with Lipofectamine Reagent (Gibco BRL, Inc.) according to the manufacturer's protocol. Cells treated only with lipofectamine or only with RNA were used as controls. After 4 hours of incubation with the lipofection mixture, the cells were washed with MEM, overlayed with MEM+FHS and incubated at 37° C. Cells were observed daily for appearance of CPE and indirect immunofluorescence was performed 48 and 72 hours post-transfection. Supernatant of transfected CRIB cells was harvested at 48 and 72 hours and inoculated in bovine testicle cells. The indicator cells were tested by IFA 24 hours after inoculation. RNA transfection efficiency was monitored by transfection of pSFVI RNA which encodes β-galactosidase followed by a X-gal assay 24 hours later (Ciccarone et al., 1993).

Liposome-mediated transfection of viral RNA in MDBK cells was followed by appearance of characteristic BVDV-induced CPE 72 hours post-transfection. Indirect immunofluorescence performed at this time confirmed the presence of BVDV antigens. Production of infectious BVD virus by CRIB cells upon RNA transfection was detected by inoculation of supernatant of these cultures in indicator bovine testicle cells. Production of infectious virus by CRIB cells after transfection with BVDV RNA was first detected 48 hours post-transfection. No infectious virus was detected in cultures treated with RNA or lipofectamine alone.

(ii) PEG-Mediated BVDV Infection of CRIB Cells

Polyethylene-glycol (PEG) is a known enhancer of infection of tissue culture cells with many viruses (Herrmann et al., 1993; Sarmiento et al., 1979; Rohde et al., 1978; Grippon et al.; 1993; Hoekstra et al. 1989; Asanaka & Lai, 1993; Sarmanti et al., 1994; Rohde et al., 1978). Thus, we sought to investigate whether PEG could have a similar effect in the BVDV/CRIB system.

CRIB-1 thru CRIB-20 and MDBK cells were trypsinized, resuspended in 1 ml of culture medium containing approximately 10 TCID50/cell of BVD virus (Singer-cp or VS115-ncp) and 5% PEG (MW 6.000, Carbowax, Fischer Sci.), and incubated one hour at 37° C. Cells were sedimented by low speed centrifugation, the medium was removed and the cell pellet was treated with warm MEM containing 37.5% PEG (MW 1.450, ATCC) as described above for cell-cell fusion. After treatment, PEG concentration was slowly reduced by addition of serum-free MEM, the cells were plated on glass coverslips and incubated at 37° C. Production of BVDV antigens in these cells was assessed by IFA performed 24 hours post-inoculation and production of progeny virus was monitored by inoculation of supernatant of these cultures in indicator bovine testicle cells followed by IFA.

For quantitation of progeny virus produced by MDBK and CRIB cells infected with Singer-cp by PEG-mediated infection, following PEG treatment cells were allowed to attach to the flask for 6 hours, washed five times with MEM to remove extracellular virus and added of culture medium. Twenty four hours after infection, the supernatant of the cultures was harvested and the amount of virus was quantitated as described above. The cells were trypsinized and submitted to IFA to estimate the percentage of BVDV infected cells. The total number of cells/flask was estimated by counting an 1:100 dilution of cell suspension in a hematocytometer chamber.

To determine the fraction of CRIB cells that is susceptible to PEG-mediated infection, we performed successive PEG-mediated infections with BVDV Singer-cp, at 72 hours intervals. At 24 hours after each round of infection, a sample of the cells was trypsinized and submitted to IFA to estimate the percentage of infected cells. The remaining cells were cultured for additional 48 hours and reinfected by PEG treatment. At the time of the subsequent infection (72 hours post infection), a fraction of cells was processed for IFA to ensure that the cells infected in the previous round had been lysed. These successive rounds of PEG-mediated infection were repeated 8 times with the same population of cells.

Addition of 5% PEG (MW 6000, Fischer Sci. ) to the virus inoculum during adsorption at 37° C. led to infection of a significant number (approximately 0.5%) of CRIB cells. The efficiency of infection was dramatically (up to 10-fold) increased when cells were treated with 37.5% PEG (MW 1450) for one minute after adsorption of virus. Neither increasing the time of exposure to 37.5% PEG nor higher PEG concentrations enhanced the infectivity further. Quantitation of progeny virus in the supernatant of CRIB cells infected with Singer-cp by PEG-mediated infection showed that these cells appear to be fully permissive to viral replication. The yield, expressed as infectious units/infected cell, was equivalent to wildtype MDBK cells (30 to 80 $TCID_{50}$), indicating that replication in individual CRIB cells reaches levels comparable to MDBK cells.

Repeated PEG-mediated infection of the same population of CRIB cells with cytopathic BVDV Singer resulted in approximately 2–3% infected cells at each round, as demonstrated by IFA performed 24 hours post-infection. Virtually all the infected cells detected at this time were lysed at 72 hours, when the subsequent round of infection was performed. At each subsequent round of infection, a similar fraction of CRIB cells was infected. These results suggest that the entire population of CRIB cells is sensitive to PEG-mediated BVDV infection at a similar level.

The results of RNA transfection and PEG-mediated infection demonstrate that the resistance resides in an early step of the viral cycle: CRIB cells are permissive to BVDV gene expression and production of infectious progeny virions if replication-competent viral genomes are introduced into cells. Further studies are being carried out to define which step of the entry process is limiting for BVDV infection in CRIB cells.

(b) Entry of Other Pestivirus

CRIB and MDBK cells were trypsinized, resuspended in MEM containing 5% PEG (MW 6000) and approximately 1 $TCID_{50}$/cell of the HCV and BDV isolates, and incubated one hour at 37° C. After PEG treatment, cells were resuspended in culture medium and incubated at 37° C. for 24 hours. Immunofluorescence for BDV or HCV antigens was performed 24 hours post-infection.

Inoculation of CRIB cells with HCV and BDV does not result in infection, as demonstrated by lack of detection of viral protein synthesis by IFA. However, inoculation of these viruses in the presence of polyethylene-glycol (PEG) results in infection of a significant number of cells. The efficiency of infection is maximized when the virus inoculum is adsorbed in the presence of 5% PEG (MW 6000), followed by treatment with 37.5 % PEG (MW 1450). PEG treatment has been associated with enhancement of virus infection in several viral systems in vitro. Although the exact mechanism by which PEG mediates infection is not well understood, it is likely enhancing the interactions between virions and the cell surface leading to increased internalization of particles. The ability of PEG to mediate infection of CRIB cells by HCV and BDV suggests that the block for viral replication is these cells is at the viral entry.

5. The Genetic Events Resulting in Resistance have not yet been Determined.

The genetic events that led to the development of the resistant phenotype remain to be determined. Two possibilities can be entertained: (1) CRIB cells are derived from BVDV and Pestivirus-resistant clones that were already present among MDBK cells, or (2) they were generated by a multistep selection process following the initial infection. In the first case, infection with cytopathic virus has operated only as a selective pressure, resulting in the selection of resistant clones. Resistant cells, if present among the MDBK population, must be at very low frequency since infection with cytolytic strains usually results in killing of virtually hundred percent of the cells and the few cells that survive normally develop a persistent infection. Alternatively, resistant cells have been generated by a multistep selection process, during persistent infection, following the initial infection. Evolution of cells through persistent infection resulting in reduced permissiveness to viral replication has been reported in other viral systems (Ron & Tal., 1986, "Spontaneous curing of a minute virus of mice carrier state by selection of cells with an intracellular block of viral replication." *J. Virol.* 58(1):26–30; Kaplan et al., 1989, "Isolation and Characterization of Hela cell Lines Blocked at Different Steps in the Poliovirus Life Cycle." J. Virol. 63:43–51; Kaplan & Racaniello, 1991, "Down Regulation of Poliovirus Receptor RMA in Hela Cells Resistant to Poliovirus Infection." *J. Virol.* 65(4):1829–35; De La Torre et al., 1988, "Coevolution of cells and viruses in a Persistent Infection of Foot-and-Mouth Disease Virus In Cell Culture." *J. Viorl.* 62(6):2050–58; Ahmed et al. 1981, "Role of host cell in a Persistent Vital Infection: Coevolution of L Cells and Reovirus During Persistent Infection." Cell 25:325–32). Long-term persistent infection of mouse L cells with a lymphotropic strain of minute virus of mice resulted in spontaneous curing of infection through selection of cell clones with an intracellular block to virus replication (Ron & Tal, 1986, supra). Hela cells partially resistant to poliovirus infection due to down-regulation of the virus receptor have been obtained through cotransfection of poliovirus genomic and subgenomic RNAs (Kaplan at al., 1989, supra; Kaplan & Racaniello, 1991, supra). Curing of late-passage CI-BHK-Rcl cells of foot and mouth disease virus (FMDV) by ribavirin treatment resulted in selection of resistant cells that have a intracellular block to virus replication (De La Torre et al., 1988, supra). Likewise, curing of mouse L cells persistently infected with reovirus by specific anti-serum resulted in mutant cells that were partially resistant to infection with wildtype virus (Ahmed et al., 1981, supra).

In our experiment, after the initial lyric infection of MDBK cells, a few cells survived and gave rise to a population of cells persistently infected with BVDV. The surviving persistently infected cells alternated periods of growth with periods of crisis in which nearly all the cells showed vacuolation and died. Therefore, it seems likely that mutations occurred during the passaging process which gave rise to mutant BVDV/Pestivirus-resistant cells that have been selected throughout the course of this persistent infection. However, we cannot rule out the possibility that a resistant cell present in the original culture was simply selected in this process. In any case, the function missing in CRIB cells that accounts for the resistance to infection by BVDV and other Pestivirus appears not to affect cell viability and growth: These cells display a pattern of growth even superior to that of the parental MDBK cells.

6. CRIB Cells are Stable

We have observed that the resistant phenotype of CRIB cells is stable: they have been cultured for over 150 population doublings and repeated BVDV inoculation experiments showed no evidence of reversion. Likewise, chemical-induced mutagenesis has also failed to induce reversion to the wildtype phenotype. The frequency of positive cells observed after inoculation of BVDV at m.o.i. higher than 50 has been estimated to be around $10^{-6}$. These occasionally infected cells seem to represent random events of infection via an alternative virus entry pathway rather than reversion to the wildtype phenotype.

7. The Resistance Exhibited by CRIB Cells is not the Result of Viral Interference Since CRIB cells originated from cells that survived lytic BVD virus infection, interference by residual replicative forms of the viral RNA would be an attractive explanation for the resistance to subsequent challenge with homologous virus. Homologous interference between cytopathic and non-cytopathic BVDV strains is a well documented phenomenon (Gillespie et al., 1962; Shirai et al., 1984). However, interference between BVD viruses is not absolute: cells infected with the ncp biotype can be superinfected with a cytopathic virus (Gillespie et al., 1962; Shirai et al., 1984). The degree of interference varies among different strains and is generally manifested by delayed replication and dampened cytopathology by the superinfecting virus (Shirai et al., 1984). The interference is believed to restrict RNA replication and assembly of progeny virions, but appears to have no effect on virus entry. CRIB cells display a degree of resistance to viral infection that greatly exceeds the levels interference resulting from homologous virus infection.

RNA transfection and PEG-mediated infection results in efficient replication of BVDV in CRIB cells as demonstrated by the amount of progeny virus recovered from the supernatant of these cultures. These findings suggest that the intracellular milieu of CRIB cells is fully permissive to BVDV replication if the virus entry block is bypassed and do not support a homologous interference mechanism as the basis for the resistance. Nonetheless, we sought to eliminate interference as a mechanistic possibility by investigating the presence of BVDV genome and gene products in these cells. Using extremely sensitive methods of detection, described above, we concluded that infectious virus or viral subproducts are absent from CRIB cells; or if present, the levels could not account for the resistant phenotype of CRIB cells.

8. The Resistance Exhibited by CRIB Cells is not the Result of a Non-Specific Anti-Viral Factor The ability of many viruses belonging to several divergent taxonomic groups to replicate in CRIB cells demonstrates that the resistant phenotype is neither a consequence of the expression of a nonspecific anti-viral factor nor a result from a broad metabolic defect in the physiologic mechanisms required for virus replication. Furthermore, the capacity of different bovine viruses to replicate in CRIB cells points out for a potential use of these cells in virology research, diagnostics and vaccine production.

The susceptibility of cells derived from fusion of CRIB and bovine lymphocytes (BL-3) to BVDV and other Pestivirus infection allows two interpretations: first, the detection of positive cells (heterokaryons) upon early post-fusion inoculation (1 to 3 days) demonstrate the absence of negative transdominant block for BVDV replication in CRIB cells; second, the detection of positive cells (heterokaryons/ hybrids) upon late inoculation post-fusion (7 to 10 days) suggests that the defect in CRIB cells can be complemented by expression of wildtype BL-3 genes. In other words, the expression of wildtype genes in the hybrids (heterokaryons) provides the factor(s) missing in CRIB cells for susceptibility to BVDV infection. Inoculation of BVDV up to 10 days after fusion was followed by detection of infected hybrids by IFA and detection of progeny virus by cocultivation. It is likely that susceptibility to infection was derived from the expression of wildtype genes from the BL-3 rather than from the presence of proteins from the original fusion partners. Experiments to obtain stable CRIB/BL-3 hybrid clones are being carried out and will help in the understanding of the genetic defects behind the resistant phenotype.

9. The Resistance Exhibited by CRIB Cells Results in a Block to Viral Entry into the Cells The ability of BVD virus to replicate in CRIB cells upon RNA transfection and PEG-mediated infection indicates that the block resides at an early stage of the viral cycle preceding translation of the open reading frame and RNA replication. The altered function likely compromises one or more of the early steps of the viral cycle, i.e. as attachment, fusion, penetration, uncoating or intracellular transport. Adsorption of the virus inoculum in the presence of PEG followed by treatment with 37.5% PEG leads to an increase in the frequency of BVDV infection in CRIB cells from $10^{-6}$ to about 5%. Thus, the PEG treatment brings about a 4.3 $\log_{10}$, increase in the efficiency of BVDV infection in CRIB cells. Testing of several different clones of CRIB cells does not alter the overall frequency of infection, ruling out any clonally-linked propensity to PEG-mediated susceptibility to infection. To determine if only a 5% fraction of the CRIB cell population is susceptible to BVDV by PEG treatment, we designed an experiment to kill all PEG-mediated BVDV susceptible cells and then use the surviving cells to perform another PEG-mediated infection. We sequentially repeated the PEG-mediated infection with BVDV Singer-cp in the same population of cells up to 8 times at intervals of 72 hours. At each cycle of infection, approximately 2 to 3% of the cells were infected and lysed, as demonstrated by IFA preformed 24 and 72 hours post-infection. Subsequent virus inoculations led to a similar number of infected cells. From these data we conclude that the surviving cell population in CRIB cultures infected with BVDV Singer-cp by PEG are just as sensitive to subsequent reinfection, indicating that the limiting factor is the PEG-mediated infection process.

Quantitation of the progeny virus produced by CRIB cells infected by PEG-mediated infection suggests that BVDV replicates efficiently in the population of cells that get infected. The amount of infectious virus present in the supernatant 24 hours after infection is consistent with efficient viral replication in a few (2 to 3%) cells. From these experiments, we conclude that CRIB cells are fully permissive to BVD virus replication if the initial block is bypassed.

The exact mechanism by which PEG is mediating infection in CRIB cells, however, is still not clear. Polyethyleneglycol treatment has been correlated with a strong enhancement of virus binding (Gripon et al., 1993; Hoekstra et al., 1989) and with virus-cell membrane fusion (Hoekstra et al., 1989; Asanaka et al., 1993; Sarmiento et al., 1979; Fehler et al., 1992; Herrmann et al., 1993; Rohde et al., 1978). PEG has been shown to induce fusion of Sendai virus with erythrocyte ghosts (Hoekstra et al., 1989), to increase efficiency of hepatitis B virus (HBV) infection of hepatocytes (Gripon et al., 1993; ASV meeting), to allow mouse hepatitis virus (MHV) (Asanaka et al., 1993) and avian sarcoma virus (Rohde et al., 1978) to initiate infection in cells lacking specific virus receptors. Herpes simplex virus type 1 (HSV-1) and bovine herpes virus type 1 (BHV-1) mutants devoid of envelope glycoproteins involved in virus penetration are able to efficiently bind to cells but only initiate infection upon addition of PEG (Fehler et al., 1992; Sarmiento et al., 1979). PEG has been shown to enhance both binding and fusion of influenza virus with erythrocytes (Herrmann et al., 1993) and has been used to enhance detection of HIV in serum of seropositive patients (Sarmanti et al., 1994). Furthermore, we have observed that adsorption of BVDV, vesicular stomatitis virus (VSV) and bovine respiratory syncytial virus (BRSV), in the presence of 5% PEG increases plaquing efficiency and virus yield in different cell lines up to 10-fold. Although PEG may be operating by a different mechanism in each viral system, it is likely that a common feature includes an enhancement of the interactions between virions and cells.

PEG is likely mediating BVDV infection of CRIB cells by favoring interactions between virions and the cell membrane resulting in a productive pathway of BVDV entry. Supporting this hypothesis, we have observed that PEG-mediated BVDV infection of CRIB cells is dramatically reduced by inhibitors of endocytosis (phenylarsine oxide) and by agents that prevent endosomal acidification (chloroquine, NH4Cl) (Flores et al. manuscript in preparation). In other words, PEG-mediated BVDV infection of CRIB cells is dependent on functional endocytosis and subsequent endosome acidification. These data suggest that PEG is favoring infection through the physiological pathway of BVD virus entry rather than creating a non-physiological mechanism (e.g. penetration by direct fusion at the cell surface). Based on these data, it can be speculated that PEG is acting either by increasing binding to cell surface molecules or by favoring a step subsequent to virus attachment that is necessary for virus internalization in CRIB cells.

The wide range of cell lineages that support the replication of BVDV in vitro suggests that the host factors required for viral replication are quite ubiquitous among these cells. The fact that BVDV replication in vivo is restricted to a few cell populations suggests that the factors required for virus replication are differentially expressed in vivo and in vitro. It is conceivable that CRIB cells lack a function at the cell surface that is responsible for the BVDV resistant phenotype. This function appears not to be essential for cell growth in normal culture conditions, since CRIB cells display a pattern of growth undistinguishable from that of the parental cells. Thus, the factor(s) missing in CRIB cells may lead to clues into the tissue tropism of BVDV.

Previous observations have suggested that different BVDV strains may use alternative cell receptors to initiate infection in bovine cells. Nonetheless, CRIB cells were selected by infection with a single virus isolate (Singer) and display resistance to all BVDV isolates tested to date. These findings suggest that a common cell surface molecule is required for all these strains to initiate infection in MDBK cells. Moreover, it is apparent that the molecule in question is required by all known viruses of the genus Pestivirus. Thus, the cell entry mechanism of Pestiviruses may display substantial levels of conservation. The identity of this molecules) and whether it is involved in initial attachment of the virions or in a subsequent step in the internalization process are currently under investigation. Characterization of this factor(s) will be an important step towards the understanding of the early interactions of BVDV with cells as well as the molecular basis of virus tropism and host range.

The Utility of Crib Cells

Pestiviruses, especially BVDV, are common contaminants of fetal bovine serum used as growth promoter for cultured cells. As a consequence, many cell lines of different species have been found contaminated with BVDV. Inadvertent BVDV contamination of tissue culture cells may interfere with virology studies as well as with virology diagnosis. Furthermore, presence of adventitious BVDV in modified-live virus vaccines produced in tissue culture cells may lead to disastrous consequences for vaccinated animals. The consequences of inadvertent BVDV contamination of animal virus vaccines have been repeatedly reported: (i) mortality of piglets born to dams vaccinated with a HCV vaccine has been attributed to the presence of contaminant BVD virus; (ii) abortion in cows vaccinated with an IBR/BRSP/PI-3 live vaccine has been associated with vaccine contamination with a non-cytopathic BVDV strain; (iii) BVDV contamination of a Pseudorabies virus vaccine has been associated with high mortality in vaccinated piglets. Surveys for BVDV contamination in animal virus vaccines commercially available in the U.S. have revealed contamination levels as high as 8%. The inadvertent contamination of cell cultures with BVDV virus also poses a problem for virology diagnosis; contamination of FBS used in a test system may lead to false-positive Pestivirus isolation by Immunocytochemical assays or other techniques. Also, inadvertent presence of BVDV in culture cells used for viral isolation may lead to false-negative isolation due to interference. Alternatively, BVDV contamination of cell cultures may interfere with other aspects of virology research.

CRIB cells combine several desired properties of a suitable cell line for different applications: (i) they are derived from MDBK cells, one of the best characterized animal cell lines, (ii) CRIB cells are mutant MDBK cells that retain most of their desirable properties; (iii) CRIB cells are susceptible to all other bovine viruses tested so far; (iv) CRIB cells are resistant to BVDV and other Pestiviruses and therefore do not amplify any Pestivirus potentially present in contaminated serum or culture medium. These characteristics point out potential uses of CRIB cells for:

1. Production of modified-live virus vaccines for other bovine viruses: the use of CRIB cells as a system for growth of these viruses (e.g. rotavirus, respiratory syncytial virus) eliminates the probability of amplification of any potential contaminating BVDV introduced inadvertently. The same principle applies to the production of any other biological product that requires the use of a cell line of bovine origin.

2. Use of CRIB cells as a differential system for viral isolation in virology diagnosis: CRIB cells are as susceptible as the parental MDBK cells to other bovine viruses of veterinary clinical relevance. MDBK cells have been largely used for viral isolation in veterinary diagnostic.

3. The use of CRIB cell in virology research ensures that a viral system developed using these cells will be free of the potential adverse effects of adventitious Pestivirus contamination.

4. The identification of the cellular factor(s) responsible for the resistance of CRIB cells to infection with Pestiviruses by using these cells for genetic complementation analysis. The expression-cloning of the BVDV factor involved in BVDV entry into cells could be carried out using these cells.

What is claimed is:

1. An isolated clonal cell line, derived from a culture of Madin-Darby Bovine Kidney cells (MDBK cells), said clonal cell line having the characteristics of the deposit made with the American Type Culture Collection SD 1831, together with those cultures and subclones of said clonal cell line which express the in vitro resistance to bovine viral diarrhea virus characteristic of the deposited clonal cell line.

2. The isolated clonal cell line of claim 1, said cell line being resistant to in vitro infection by Bovine Viral Diarrhea Virus, Hog Cholera Virus, and Border Disease Virus, which resistance can be overcome by fusion of the cells with bovine lymphocyte cells containing wild type genes or by transfection with viral RNA, and those cultures and subclones of said clonal cell line which express resistance to in vitro infection by Bovine Viral Diarrhea Virus and all other known Pestiviruses, which resistance can be overcome by fusion of the cells with bovine lymphocyte cells containing wild type genes or by transfection with viral RNA.

3. An isolated clonal cell line derived from a culture of Madin-Darby Bovine Kidney Cells (MDBK cells), and those cultures and subclones of said clonal cell line, consisting of cells characterized as follows:

(a) the cells are resistant to in vitro infection by all biotypes and strains of Bovine Viral Diarrhea Virus (BVDV) Hog Cholera Virus (HCV), and Border Disease (BDV);
(b) the cells are susceptible to infection by other unrelated viruses that replicate in bovine kidney cells;
(c) the cells have a genetic defect which is both stable and recessive and which confers resistance to in vitro BVDV infection at the level of viral entry, and not by intracellular block to viral replication;
(d) the cells have an intracellular milieu fully permissive to replication of BVDV and other viruses that gain entry into the cells; and
(e) the genetic defect conferring resistance to in vitro BVDV infection does not impair cell growth and viability.

4. The isolated clonal cell line of claim 3, wherein said cells are susceptile to bovine herpes type 1, 2 and 4, bovine adenovirus type 3, vesicular stomatitis virus, bovine parvovirus, bovine respiratory syncytial virus, bovine enterovirus and bovine parainfluenza virus.

* * * * *